United States Patent
Fiorillo et al.

(10) Patent No.: US 11,903,687 B2
(45) Date of Patent: Feb. 20, 2024

(54) TRIBOELECTRIC WEARABLE DEVICE AND METHOD FOR PHYSIOLOGICAL MONITORING

(71) Applicant: UNIVERSITA' DEGLI STUDI MAGNA GRAECIA DI CATANZARO, Catanzaro (IT)

(72) Inventors: Antonino Secondo Fiorillo, Reggio di Calabria (IT); Salvatore Andrea Pullano, Catanzaro (IT); Costantino Davide Critello, Catanzaro (IT)

(73) Assignee: UNIVERSITA' DEGLI STUDI MAGNA GRAECIA DI CATANZARO, Catanzaro (IT)

( * ) Notice: Subject to any disclaimer, the term of this patent is extended or adjusted under 35 U.S.C. 154(b) by 589 days.

(21) Appl. No.: 16/775,065

(22) Filed: Jan. 28, 2020

(65) Prior Publication Data
US 2021/0228097 A1    Jul. 29, 2021

(51) Int. Cl.
*A61B 5/0265*   (2006.01)
*A61B 5/00*   (2006.01)
(Continued)

(52) U.S. Cl.
CPC ............ *A61B 5/0265* (2013.01); *A61B 5/029* (2013.01); *A61B 5/0295* (2013.01); *A61B 5/681* (2013.01)

(58) Field of Classification Search
CPC ..... A61B 5/0265; A61B 5/029; A61B 5/0295; A61B 5/681; A61B 5/7239
See application file for complete search history.

(56) References Cited

U.S. PATENT DOCUMENTS

2004/0220485 A1* 11/2004 Rytky ............... A61B 5/02438
                                                                  600/509
2008/0077026 A1*  3/2008 Banet .................... A61B 5/327
                                                                  600/509
(Continued)

FOREIGN PATENT DOCUMENTS

CN    205951381 U      2/2017
WO    2007079288 A1   12/2007
WO    2018107738 A1    6/2018

OTHER PUBLICATIONS

Salvatore A. Pullano, C.D. Critello Antonino S. Fiorillo, "Triboelectric-Induced Pseudo-ICG for Cardiovascular Risk Assessment on Flexible Electronics" published on Sciencedirect.com Nov. 6, 2019.

*Primary Examiner* — Eric F Winakur
*Assistant Examiner* — Abid A Mustansir
(74) *Attorney, Agent, or Firm* — Dennemeyer & Associates LLC

(57) ABSTRACT

A triboelectric wearable device (100) and a method for physiological monitoring, comprising:
  a support element (101);
  a first element (102) consisting of a first metallic contact (102a) and a second metallic contact (102b) between which is placed a dielectric layer, said first element (102) being able to be placed in contact with a wrist (50) of a user and bonded to the support element (101);
  a second element (103) overlapped and bonded to the first element (102) and to the support element (101).

The triboelectric wearable device (100) further comprises an electronic interface (104) for acquiring and processing the signal generated by means of the triboelectric effect in the blood vessels of the user near the wrist (50), said electronic interface (104) being housed into the support element (101)

(Continued)

and connected to the first metallic contact (102*a*) and to the second metallic contact (102*b*) of the first element (102).

7 Claims, 6 Drawing Sheets

(51) Int. Cl.
    *A61B 5/029*     (2006.01)
    *A61B 5/0295*     (2006.01)

(56) References Cited

U.S. PATENT DOCUMENTS

| | | | |
|---|---|---|---|
| 2017/0020413 A1* | 1/2017 | Otaka | A61B 5/6814 |
| 2021/0113132 A1* | 4/2021 | Bhagat | A61B 5/28 |
| 2021/0208624 A1* | 7/2021 | Kim | A61B 5/681 |

* cited by examiner

TRIBOELECTRIC WEARABLE DEVICE AND METHOD FOR PHYSIOLOGICAL MONITORING

BACKGROUND

The present disclosure relates to a triboelectric wearable device for physiological monitoring.

The present disclosure relates also to a method for physiological monitoring.

In particular, the present disclosure relates to a triboelectric wearable device and method for physiological monitoring, of the type comprising sensors and electronics configured to acquire and process the signals generated by said sensors.

The reference technical field is the electromedical sector, specifically sensors and electronics for acquiring and processing biomedical signals concerning the cardiac activity.

Regarding this latter context, hemodynamic parameters such as pre-ejection period (PEP), left ventricular ejection time (LVET), stroke volume (SV) and cardiac output (CO) provide greater insight into the pathophysiology of cardiovascular diseases. Hemodynamic parameters assessment is particularly important in a health care setting, for monitoring patients with significant underlying cardiovascular conditions, for diagnostic and therapeutic purposes, so as to be able to identify the most appropriate interventional treatment. The methods clinically used for the detection of the aforementioned parameters are characterized by a marked invasiveness for the patient, for example by using a catheter for thermodilution applications, with significant inconveniences for the safety of the patient.

The impedance cardiography, on the other hand, has emerged as a unique and highly accurate non-invasive technique that exploits the measurement of the characteristic impedance of the tissues, or bioimpedance, at the thoracic segment (i.e. neck and chest) or limbs during the passage of a low intensity alternate current applied by means of a pair of electrodes, with a second pair of electrodes detecting the resulting potential difference. The application of the generalized Ohm's law $\bar{V}=\bar{Z}*\bar{I}$, in short, allows to obtain the bioimpedance '$\bar{Z}$' by measuring the aforementioned induced potential difference. In a broader sense, the bioimpedance is a quantity that is not easy to detect and is a function of time, $Z(t)$, and said bioimpedance, together with its variation with respect to the baseline, the first and second derivatives with respect to time, respectively $\Delta Z$, $dZ/dt$ e $d^2Z/dt^2$, is often referred by means of the acronym ICG, or impedance cardiography. Despite not being invasive, this measurement procedure may not be applicable on patients in an unconscious state or not collaborative, giving rise to the need to perform surveys through alternative methods. Also, invasive techniques for hemodynamic parameters monitoring are not always feasible in the routine care of patients with cardiovascular diseases.

As it is known, the triboelectric effect, is a contact-electrification phenomenon and consists in the production of electrical charges on surfaces, due to a physical contact between two different materials.

Several devices that exploit the inherent high output voltage and low current generated by the triboelectric effect, used in the biomedical sector, are currently known.

A first example of known device exploiting the triboelectric effect is described by the international application WO2018107738 that discloses a triboelectric sensor testing device simulating a vital sign, the device comprising a first frame, a sample table and a first airbag provided on the first frame, wherein an accommodating space is formed between the sample table and the first airbag. A triboelectric sensor can be disposed in the accommodating space, and an air drive unit connected to the first airbag. The air drive unit is configured to repeatedly increase or decrease the amount of air in the first airbag, so that two contact surfaces of the triboelectric sensor can come in contact or separated from each other, providing the triboelectric sensor with a test condition close to a vital sign.

Still, the international application WO2007079288 describes the mechanical activity of a heart, sensed by a cardiac lead that carries a triboelectric sensor that produces a signal in response to cardiac contractions. A lead fabricated according to the disclosure can be used for a variety of purposes, including pacing capture verification, electromechanical conductivity status of the myocardium, such as detecting relatively reduced myocardial activity indicative of ischemia, myocyte necrosis, arterial stenosis and the like. The sensor allows detection of mechanical activity without signal blanking traditionally utilized to stimulate and sense the cardiac activity. Traditional circuitry can be employed to stimulate/sense while a triboelectric sensor unit detects evoked and/or intrinsic mechanical cardiac activity. A reduction from a prior amplitude signal can be used to set patient or clinician alert signals, set a logical flag regarding possible lead dislodgement, compare prior and current signals, store same in memory, and/or provide via telemetry for display.

Finally, the utility model patent CN205951381 discloses a thin polymer film and triboelectric pressure sensor, wherein the thin film has a first surface that is used as the triboelectric pressure sensor's frictional interface, and is equipped with a structure protruding on said surface. The polymer has a second surface suitable for use as a friction area for the triboelectric sensor, and at least two types of protrusions.

However, the known systems such as those described does and above, suffer from intrinsic limitations, e.g. not providing impedance cardiography-related information, the presence of moving parts, and also the more or less accentuated invasiveness of the sensors and devices in general designed to evaluate the reference physiological parameters.

An object of the present disclosure is to provide a triboelectric wearable device and a method for physiological monitoring that do not include moving parts and that allow reliable and non-invasive measurements of a biomedical signal related to the cardiac activity having, therefore, characteristics so that to overcome the limits that still affect the currents devices, with reference to the known technique.

Another object of the present disclosure is to provide a triboelectric wearable device and a method for physiological monitoring that allow to detect the aforementioned biomedical signal in order to evaluate hemodynamic parameters useful for diagnostic and therapeutic cardiovascular investigations on a user.

According to the present disclosure, an improved triboelectric wearable device for physiological monitoring is provided.

According to the present disclosure, an improved method for physiological monitoring is provided.

BRIEF DESCRIPTION OF THE DRAWINGS

For a better understanding of the present disclosure a preferred embodiment is now described, purely by way of a non-limiting example, with reference to the annexed drawings, in which.

Figure 1:
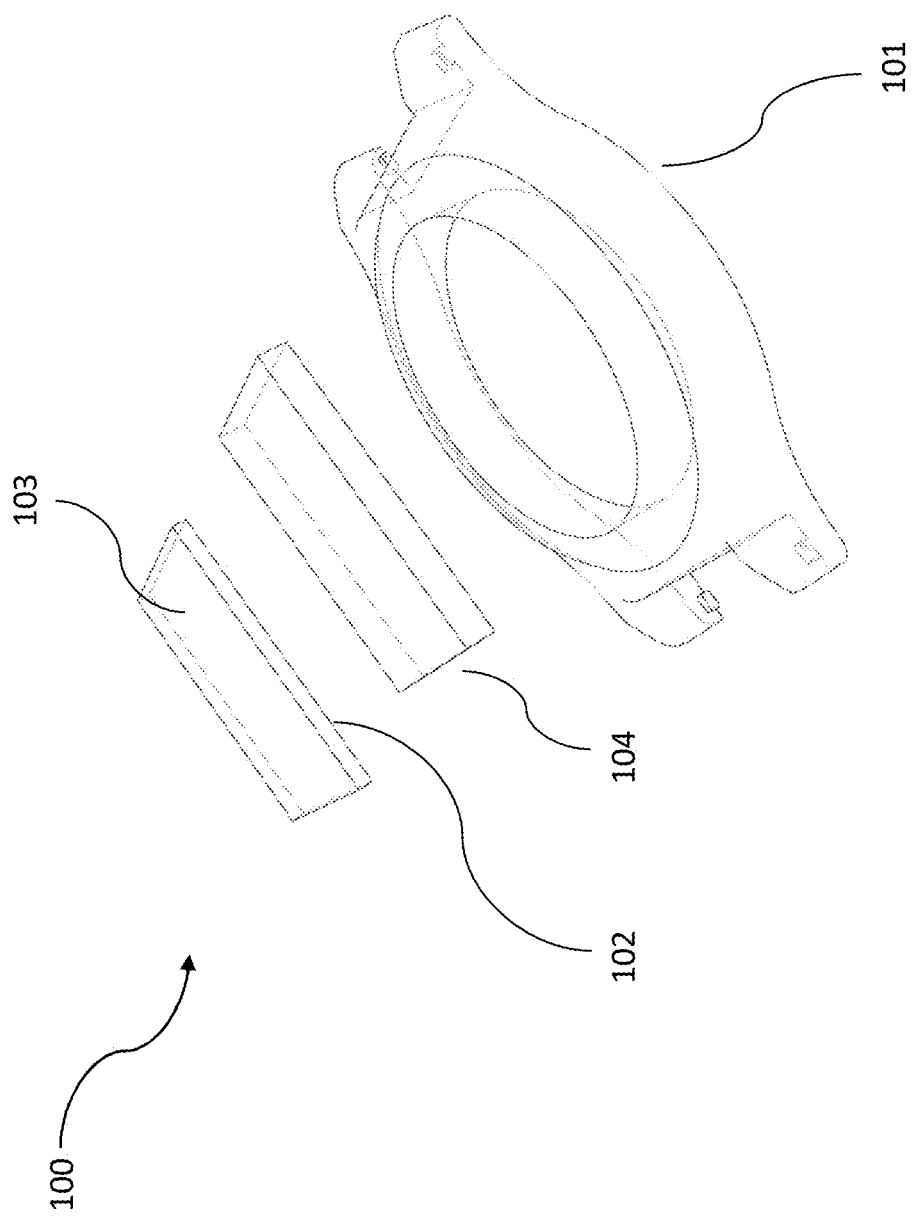
FIG. 1 shows an overall view of a triboelectric wearable device for physiological monitoring, according to an embodiment of the disclosure.

With reference to these figures and, in particular, to FIG. 1, a triboelectric wearable device for physiological monitoring is shown, according to the disclosure.

DETAILED DESCRIPTION OF THE DRAWINGS

In particular, the triboelectric wearable device 100 for evaluating physiologic parameters, comprises:
  a support element 101;
  a first element 102 consisting of a first metallic contact 102a and a second metallic contact 102b between which is placed a dielectric layer;
  a second element 103 overlapped and bonded to the first element 102 and to the support element 101.

According to an aspect of the disclosure, the first element 102 is able to be placed in contact with a wrist 50 of a user and is bonded to the support element 101.

According to an aspect of the disclosure, the triboelectric wearable device 100 comprises an electronic interface 104 for acquiring and processing the signal, generated through the triboelectric effect in the blood vessels of the user, acquired near the wrist 50.

According to an aspect of the disclosure, the electronic interface 104 is connected to the first metallic contact 102a and to the second metallic terminal 102b of the first element 102.

According to another aspect of the disclosure, the first element 102 and the electronic interface 104 are electrically connected by means of a coaxial cable, said coaxial cable being connected to the first metallic contact 102a and to the second metallic contact 102b.

Figure 3:
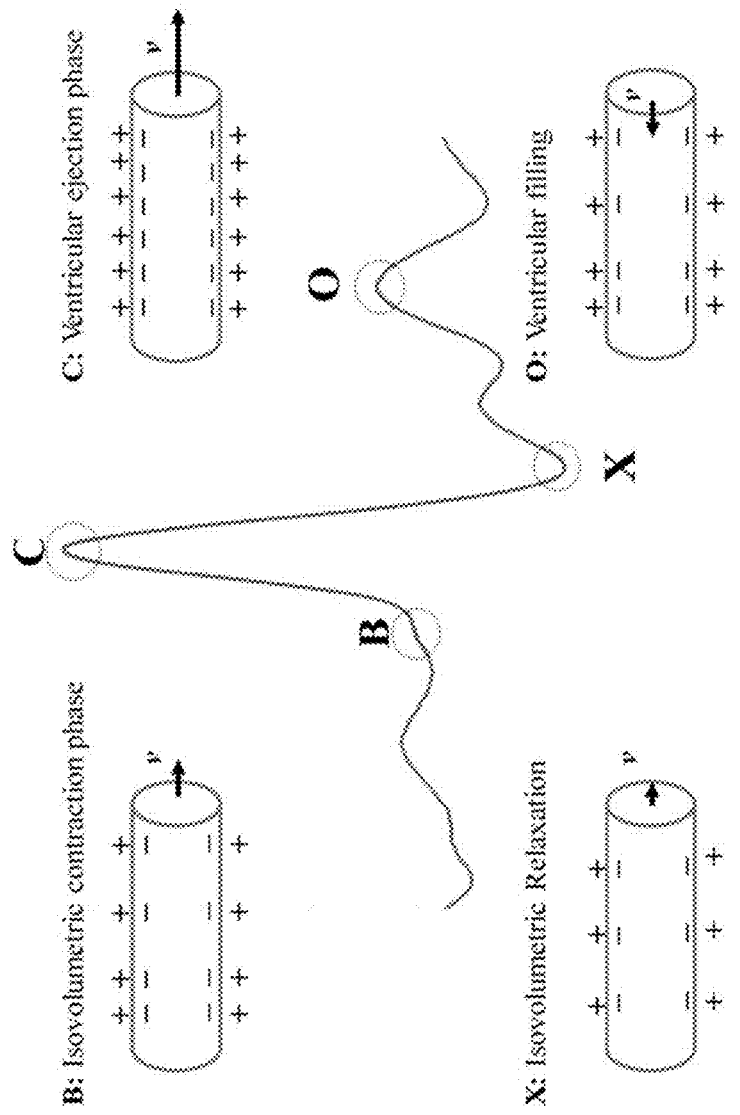
FIG. 3 shows a graph of dZ/dt in which each phase of the cardiac activity is related to the triboelectric charge produced onto the endothelial vessel, according to the disclosure.
Figure 4:
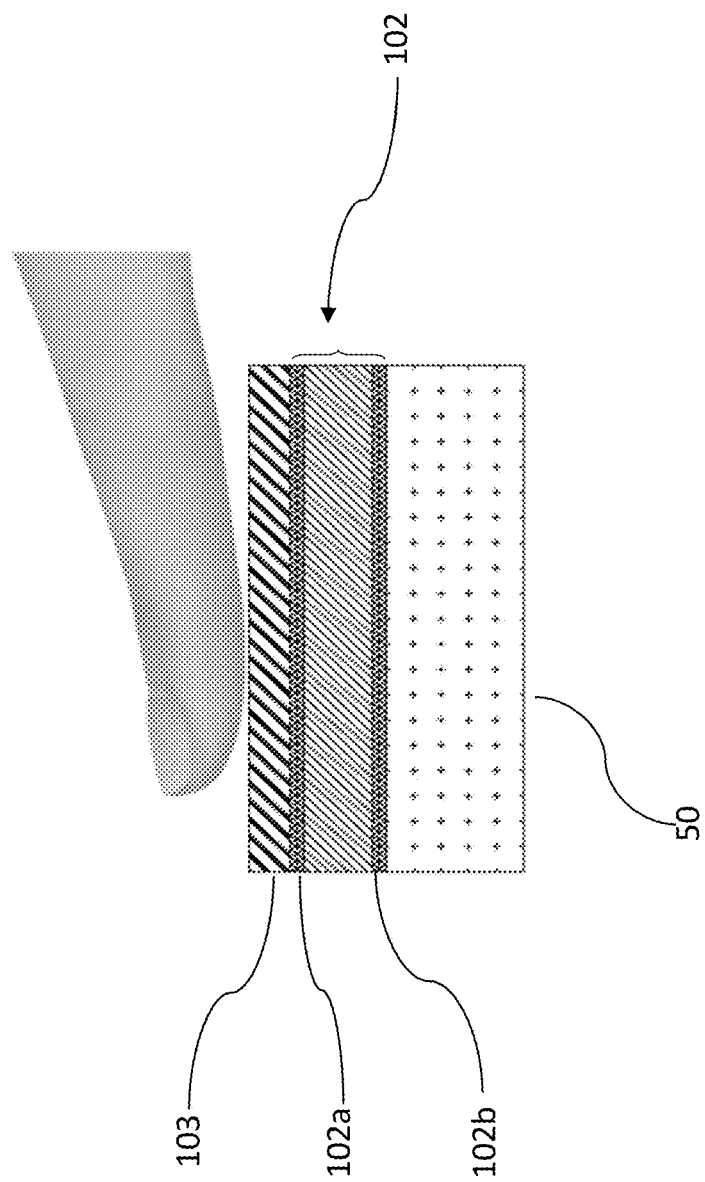
FIG. 4 shows a section of a transducer element of the triboelectric wearable device physiological monitoring applied to a user, according to the disclosure.

As previously described, the scope of the present disclosure is to provide a wearable device and a method to evaluate impedance cardiography (ICG) signals avoiding the original concept of bioimpedance, more precisely evaluating the first derivative with respect to time of said ICG and, indirectly, being able to evaluate the other components of the ICG (i.e. $\Delta Z$, $d^2Z/dt^2$). Such a purpose is achieved exploiting the triboelectric effect generated by the friction between corpuscles, for example the erythrocytes, or red blood cells, platelets, leukocytes, and proteins that flow in the blood vessels of the user/patient, and the internal walls of said vessels. According to FIG. 3, dZ/dt waveform in the ICG analysis is related to the acceleration of the blood and is characterized by four focal points, corresponding to the cardiac cycle: the "B point" (opening of the aortic valve), the "C-point" (the peak blood flow in the aorta), the "X-point" (closing of the aortic valve), and the "O-point" (opening of the mitral valve). The left ventricular ejection time is directly derived from dZ/dt and is equal to the time interval between B and X. LVET, together with the amplitude of the C-point, is used to evaluate SV using the Kubicek equation.

In particular, according to an aspect of the disclosure, the measurement of the related biomedical signal, or pseudo-ICG signal in that it is attributable to said signal and in particular to the first derivative with respect to time dZ/dt, like known ICG measurements, it is performed in correspondence with the blood vessels of the wrist 50, preferably at the level of the arteries and more precisely near the radial artery.

Figure 5:
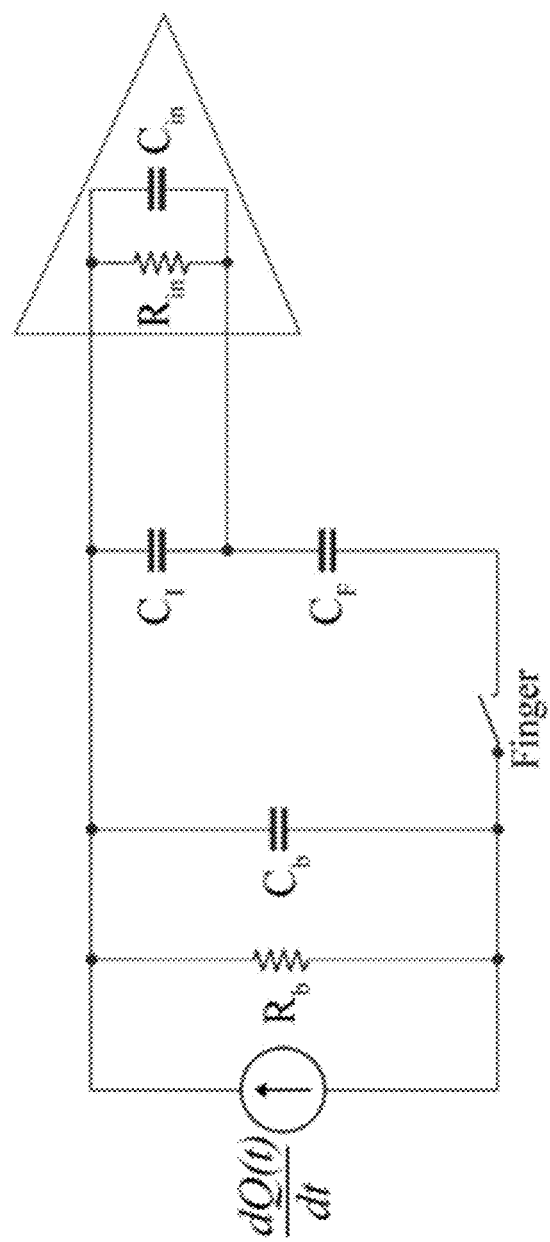
FIG. 5 shows an equivalent circuit of the transducer elements and an acquiring electronic interface of the triboelectric wearable device for physiological monitoring applied to a user according to the disclosure, including an equivalent electrical model of the human body.
Figure 6:
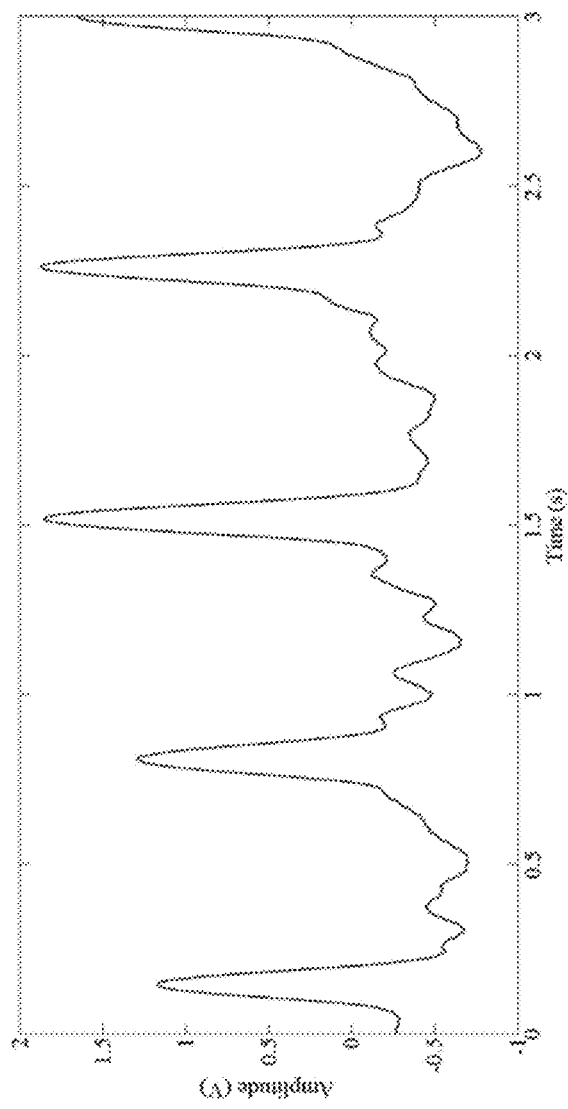
FIG. 6 shows a graph of a biomedical signal acquired through the triboelectric wearable device for physiological monitoring, according to the disclosure.

Starting from the assumption, and as documented in the literature, that at the level of the blood tracts, the inner part of the vessel is characterized by an electrical bottle brush structure, including the lipid bilayer at the top, and the branching trees of negative charges, triboelectricity occurs between the cell corpuscles and the walls of the blood vessels, the Applicant designed and implemented a wearable device comprising the sensing first element 102 consisting of a metal thin film strip, coupled to the second element 103 made of a dielectric thin film, for example made of a plastic material. The overall device, including the electrical model of the body, the first element 102, connected to the electronic interface 104 is schematized in FIG. 5. In order to acquire and process the detected bio-signal, the first element 102 is positioned at the radial level of the wrist and together with the dielectric element forms a capacitive voltage divider, by which it is possible to efficiently evaluate the bioelectric potential, as shown in FIG. 6, through the acquiring electronic interface 104, for example an analog or a digital oscilloscope.

Figure 2:
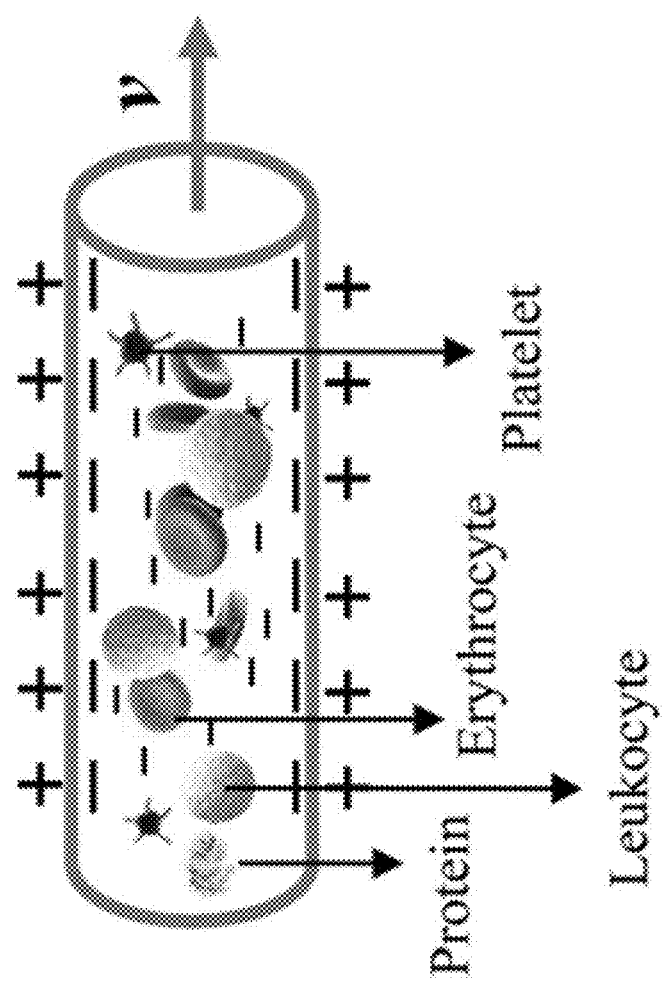
FIG. 2 shows a graphic schematization of the triboelectric effect inside the circulatory stream with the relative arrangement of electrical charges on the internal and external walls of an endothelial vessel, an effect caused by the friction between blood components having a non-zero net charge and the internal walls of said vessel, during a cardiac cycle and depending on hemodynamic parameters such as speed and acceleration.

In particular, the triboelectric charge generation profile on the outer surface of the endothelial vessel in question is related to the acceleration of the fluid inside the circulatory stream, 'v', as shown in FIG. 2, and therefore is related to the first derivative of the impedance, dZ/dt.

Such an approach, performed by the Applicant, allows to perform an indirect measurement of the ICG in a non-invasive way and by means of passive sensor, in the absence of alternate current sources, electrodes applied to the user and electronics for acquiring and processing the potential difference generated by the injected alternate current, which represent limits of the known systems used in impedance cardiography. According to another aspect of the disclosure, the dielectric layer interposed between the first metallic contact 102a and the second metallic contact 102b consists of a polymeric thin film, preferably made of polyvinylidene fluoride (PVDF).

According to another aspect of the disclosure, the second element 103 employed as a friction surface, bonded to the first element 102, consists of a dielectric polymeric thin film, preferably made of polyethylene terephthalate (PET).

Advantageously according to the disclosure, overlapping the second element 103 on the first element 102 implements a capacitive coupling capable of detecting the electrical charge outside the blood vessels deriving from the friction between blood corpuscles and the wall of the vascular ducts.

According to an aspect of the disclosure, the electronic interface 104 for acquiring the signal generated through the triboelectric effect is an electronic circuit able to acquire, filter and process said signal.

According to another aspect of the disclosure, the support element 101 is the case of a wristwatch, preferably made of a shielded metallic material.

Advantageously according to the disclosure, implementing the measurements of the biomedical signal generated through the triboelectric effect by the triboelectric wearable device 100, and in particular by the first element 102 and the second element 103, allows not to cause discomfort to the user, also thanks to the absence of moving parts.

Advantageously according to the disclosure, the use of the triboelectric wearable device 100 allows to evaluate, in a non-invasive way, parameters concerning the cardiac activity of the user, such as stroke volume and cardiac output.

According to the present disclosure a method for physiological monitoring by means of the triboelectric wearable device 100 is also provided, comprising the steps:
- of placing the triboelectric wearable device 100 over a wrist 50 of a user near the radial artery placing the first element 102 in contact with the skin of the user;
- of closing an equivalent electrical circuit whose branches consist of the triboelectric wearable device 100 and the body of the user placing at least a finger of a hand, said hand being different from the hand near which the triboelectric wearable device 100 is placed, in contact with the second element 103;
- of acquiring the electrical pseudo-ICG signal generated by means of the triboelectric effect between corpuscles in motion into blood vessels of the user and the walls of said vessels, the electrical signal being detected by the triboelectric wearable device 100 by means of a system 104 consisting of electronic parts and connected to two contacts of the first element 102.

Therefore, the triboelectric wearable device and method for physiological monitoring according to the disclosure allow an effective and non-invasive measure of cardiac activity and in particular of a pseudo-ICG biomedical signal, i.e. concerning impedance cardiography.

In addition, the triboelectric wearable device for physiological monitoring according to the disclosure allows to detect directly, without the use of mathematical formulas, the aforementioned biomedical signal related to the thoracic impedance, and in particular to the first derivative dZ/dt of said thoracic impedance. By using mathematical calculations applied to bio-signal, or pseudo-ICG signal, detected by means of the triboelectric wearable device, on the contrary, it is possible to evaluate indirectly, the other components of the ICG.

Another advantage of the triboelectric wearable device for physiological monitoring according to the disclosure is that ensure a high safety to the user, with reference to the known systems for detecting the ICG signal.

A further advantage of the triboelectric wearable device for physiological monitoring according to the disclosure is not expensive and is easy to prototype and industrialize.

Still, the triboelectric wearable device for physiological monitoring according to the disclosure is of ease use.

It is finally clear that the triboelectric wearable device for physiological monitoring described and illustrated herein can be subject to modifications and variations without departing from the protective scope of the present disclosure, as defined herein.

Reference throughout this specification to "the embodiment," "this embodiment," "the previous embodiment," "one embodiment," "an embodiment," "a preferred embodiment" "another preferred embodiment" or similar language means that a particular feature, structure, or characteristic described in connection with the embodiment is included in at least one embodiment of the present disclosure. Thus, appearances of the phrases "in the embodiment, "in this embodiment," "in the previous embodiment, in one embodiment, in an embodiment," "in a preferred embodiment," "in another preferred embodiment," and similar language throughout this specification may, but do not necessarily, all refer to the same embodiment.

The described features, advantages, and characteristics of the invention may be combined in any suitable manner in one or more embodiments. One skilled in the relevant art will recognize that the details of the disclosure may be practiced without one or more of the specific features or advantages of a particular embodiment. In other instances, additional features and advantages may be recognized in certain embodiments that may not be present in all embodiments of the disclosure. While the present disclosure has been described in connection with certain exemplary or specific embodiments, it is to be understood that the disclosure is not limited to the disclosed embodiments, but, on the contrary, is intended to cover various modifications, alternatives, modifications and equivalent arrangement as will be apparent to those skilled in the art. Any such changes, modifications, alternative, equivalents and the like may be made without departing from the spirit and scope of the disclosure.

The invention claimed is:

1. A wearable device for physiological monitoring, comprising:
    a support element;
    a first element consisting of a first metallic contact and a second metallic contact between which is placed a dielectric layer, said first element configured to be placed in contact with a wrist of a user and bonded to the support element;
    a second element overlapped and bonded to the first element and to the support element; and
    an electronic interface for acquiring and processing a signal generated by means of a triboelectric effect in a radial arterial blood vessel of a user near a wrist, said electronic interface being housed within the support element and connected to the first metallic contact and to the second metallic contact of the first element.

2. The wearable device according to claim 1, wherein said dielectric layer placed between the first metallic contact and the second metallic contact is composed of a polymer thin film made of PVDF.

3. The wearable device according to claim 1, wherein the second element bonded to the first element is composed of a dielectric polymer thin film made of PET.

4. The wearable device according to claim 1, wherein the first element and the electronic interface are electrically connected by means of a coaxial cable, said coaxial cable being connected to the first metallic contact and to the second metallic contact.

5. The wearable device according to claim 1, wherein the electronic interface for acquiring the signal generated by means of the triboelectric effect is an electronic circuit able to acquire, amplify, filter and process said signal.

6. The wearable device according to claim 1, wherein the support element is the case of a wristwatch.

7. A method for physiological monitoring by means of the device according to one of claims 1-5, comprising the steps of:

placing the triboelectric wearable device over the wrist of the user near the radial artery placing the first element in contact with the skin of the user;

closing an equivalent electrical circuit whose branches consist of the triboelectric wearable device and the body of the user placing at least a finger of a hand, said hand being different from the hand near which the triboelectric wearable device is placed, in contact with the second element;

acquiring the electrical signal generated by means of the triboelectric effect between corpuscles in motion into blood vessels of the user and the walls of said vessels, the electrical signal being detected by the triboelectric wearable device by means of a system consisting of electronic parts and connected to two contacts of the first element.

* * * * *